(12) United States Patent
Ozawa et al.

(10) Patent No.: US 9,205,178 B2
(45) Date of Patent: Dec. 8, 2015

(54) TI-NI-NB ALLOY DEVICE

(75) Inventors: Michihide Ozawa, Sendai (JP); Kiyoshi Yamauchi, Sendai (JP); Yuji Sutou, Sendai (JP); Takamitsu Takagi, Sendai (JP); Shuzou Yamashita, Okayama (JP); Kouji Mori, Okayama (JP)

(73) Assignees: NEC TOKIN CORPORATION, Miyagi (JP); TOHOKU UNIVERSITY, Miyagi (JP)

( * ) Notice: Subject to any disclaimer, the term of this patent is extended or adjusted under 35 U.S.C. 154(b) by 1136 days.

(21) Appl. No.: 11/915,130

(22) PCT Filed: May 23, 2006

(86) PCT No.: PCT/JP2006/310199
§ 371 (c)(1),
(2), (4) Date: Feb. 5, 2008

(87) PCT Pub. No.: WO2006/126515
PCT Pub. Date: Nov. 30, 2006

(65) Prior Publication Data
US 2009/0068054 A1    Mar. 12, 2009

(30) Foreign Application Priority Data
May 23, 2005 (JP) ................................. 2005-149342

(51) Int. Cl.
| A61L 31/02 | (2006.01) |
| A61L 31/14 | (2006.01) |
| C22C 1/00 | (2006.01) |
| C22C 19/00 | (2006.01) |
| C22C 19/03 | (2006.01) |
| C22C 30/00 | (2006.01) |
| C22F 1/00 | (2006.01) |
| C22F 1/10 | (2006.01) |

(52) U.S. Cl.
CPC ............... *A61L 31/022* (2013.01); *A61L 31/14* (2013.01); *C22C 1/00* (2013.01); *C22C 19/005* (2013.01); *C22C 19/03* (2013.01); *C22C 30/00* (2013.01); *C22F 1/006* (2013.01); *C22F 1/10* (2013.01); *A61L 2400/16* (2013.01)

(58) Field of Classification Search
CPC ... A61L 31/022; A61L 31/14; A61L 2400/16; C22C 14/00; C22C 1/00; C22C 19/005; C22C 19/03; C22C 30/00; C22F 1/006; C22F 1/10
USPC ................. 420/421, 417, 584, 580, 581, 588
See application file for complete search history.

(56) References Cited

U.S. PATENT DOCUMENTS

| 3,174,851 | A | 3/1965 | Buehler et al. |
| 4,631,094 | A * | 12/1986 | Simpson et al. .............. 148/563 |
| 4,770,725 | A | 9/1988 | Simpson et al. |
| 4,894,100 | A | 1/1990 | Yamauchi et al. |
| 5,441,515 | A | 8/1995 | Khosravi et al. |
| 5,601,593 | A | 2/1997 | Freitag |
| 5,618,299 | A | 4/1997 | Khosravi et al. |
| 5,667,522 | A | 9/1997 | Flomenblit et al. |
| 6,159,238 | B1 | 12/2000 | Killion et al. |
| 6,312,455 | B2 | 11/2001 | Duerig et al. |
| 6,451,052 | B1 | 9/2002 | Burmeister et al. |
| 6,485,507 | B1 | 11/2002 | Walak et al. |
| 6,582,461 | B1 | 6/2003 | Burmeister et al. |
| 6,610,046 | B1 * | 8/2003 | Usami et al. .................. 604/530 |
| 6,652,576 | B1 | 11/2003 | Stalker |
| 6,682,608 | B2 * | 1/2004 | Abrams et al. ................ 148/402 |
| 6,719,781 | B1 | 4/2004 | Kim |
| 6,997,947 | B2 | 2/2006 | Walak et al. |
| 7,632,303 | B1 | 12/2009 | Stalker et al. |
| 2001/0007953 | A1 | 7/2001 | Duerig et al. |
| 2004/0193257 | A1* | 9/2004 | Wu et al. ....................... 623/1.46 |
| 2005/0096733 | A1 | 5/2005 | Kovneristy et al. |
| 2005/0209683 | A1 | 9/2005 | Yamauchi et al. |
| 2007/0044868 | A1 | 3/2007 | Yamauchi et al. |
| 2009/0062906 | A1 | 3/2009 | Ozawa et al. |

FOREIGN PATENT DOCUMENTS

| JP | 58-161753 A | 9/1983 |
| JP | 63-14834 A | 1/1988 |
| JP | 63-014835 A | 1/1988 |
| JP | 63-171844 A | 7/1988 |
| JP | 03-268749 A | 11/1991 |
| JP | 05-295498 A | 11/1993 |
| JP | 07-252553 A | 10/1995 |
| JP | 10-500595 A | 1/1998 |
| JP | 11-42283 A | 2/1999 |
| JP | 11-99207 A | 4/1999 |
| JP | 2003-102849 A | 4/2003 |
| JP | 2004-321348 A | 1/2004 |
| WO | WO 1995/27092 A1 | 10/1995 |
| WO | WO 2004/017865 A1 | 3/2004 |

OTHER PUBLICATIONS

He et al., "TiNiNb Wide Hysteresis Shape Memory Alloy with Low Niobium Content", Materials Science and Engineering A, 2004, Elsevier, 371, p. 193-197.*
T. Takagi et al., "Chodansei Ti-Ni-Nb Gokin no Gyakuhentai Kyodo ni Oyobosu Yowai Koka", The Japan Institute of Metals Koen Gaiyo, vol. 136, Mar. 29, 2005, p. 403.
M. Ozawa et al., "Ti-Ni-kei Keijo Kioku Gokin ni Okeru Reikan Kako ni Oyobosu Nb Tenkaryo to Hentai Ondo no Eikyo", Nippon Kikai Gakkai Zairyo Rikigaku Bumon Koenkai Koen Ronbunshu, vols. 507-508, Jul. 20, 2004, pp. 507-508.

(Continued)

*Primary Examiner* — Roy King
*Assistant Examiner* — Caitlin Kiechle
(74) *Attorney, Agent, or Firm* — Holtz, Holtz, Goodman & Chick PC

(57) ABSTRACT

A Ti—Ni—Nb alloy device is provided which is a shape memory device excellent in response characteristics. The Ti—Ni—Nb alloy device is made of a Ti—Ni—Nb alloy which finishes transformation at a temperature lower than 10° C. after start of reverse transformation.

11 Claims, 1 Drawing Sheet

(56) References Cited

OTHER PUBLICATIONS

English Language International Search Report dated Jul. 4, 2006, in connection to Application No. PCT/JP2006/310199.
D. Goldstein et al., "Nitinol-Based Fuze Arming Component", NSWC TR 88-340 (1988).
K. Otsuka et al., "Shape Memory Materials", 1998, Cambridge University Press, pp. 254-26.
International Preliminary Report on Patentability and Written Opinion of the International Searching Authority dated Nov. 23, 2007, issued in connection with International Application Serial No. PCT/JP2006/310199.
M. Ozawa, et al., "Stent with Autonomic Function", U.S. Appl. No. 11/915,070, filed Feb. 5, 2009.
U.S. Appl. No. 11/915,070; First Named Inventor: Michihide Ozawa ;Title: "Stent with autonomic function"; Filed: Feb. 5, 2008.

* cited by examiner

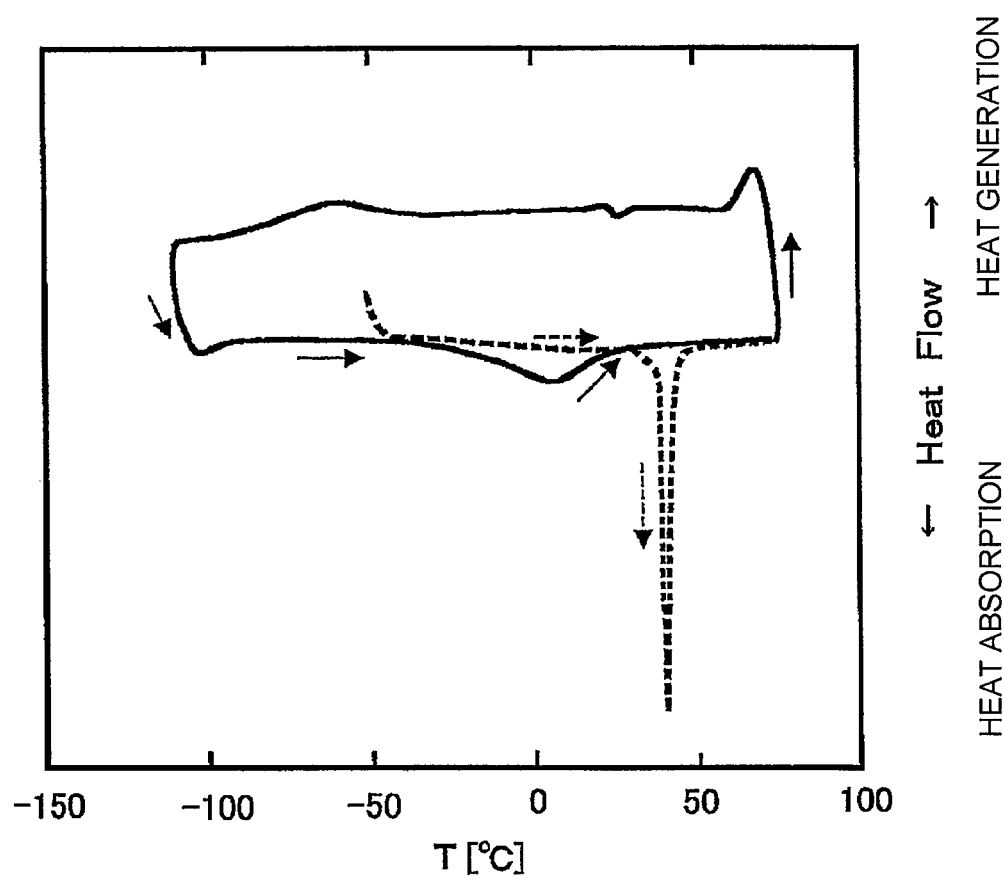

TI-NI-NB ALLOY DEVICE

TECHNICAL FIELD

This invention relates to a shape memory device excellent in response characteristics to an external environment temperature and, in particular, to a high-temperature operating device required to operate at a temperature not lower than 100° C. and a biomedical material.

BACKGROUND ART

As well known, a shape memory alloy, such as a Ti—Ni alloy, exhibits a remarkable shape memory effect in association with martensitic reverse transformation. Further, the shape memory alloy exhibits excellent superelasticity in association with stress-induced martensitic transformation induced by strong deformation in a parent phase after the reverse transformation. The superelasticity is observed in a number of shape memory alloys and, among others, is particularly remarkable in the Ti—Ni alloy and a Ti—Ni—X alloy (X=V, Cr, Co, Nb, or the like).

The shape memory effect of the Ti—Ni alloy is disclosed in Patent Document 1. The superelasticity is disclosed in Patent Document 2. The shape memory effect and the superelasticity of the Ti—Ni—X alloy are described, for example, in Patent Documents 3 and 4 for a Ti—Ni—V alloy and in Patent Document 5 for a Ti—Ni—Nb alloy.

As compared with the Ti—Ni alloy, the Ti—Ni—Nb alloy exhibits a characteristic that temperature hysteresis of stresses is increased by applying a stress. Therefore, the Ti—Ni—Nb alloy is put into practical use as a joint for reactor piping.

Stent treatment is a new technique rapidly put into use in recent years. The stent is a mesh-like metal tube to be placed in a living body in order to prevent renarrowing or restenosis of a narrow portion, such as a blood vessel, after it is expanded. The stent is reduced in diameter and received in an end portion of a catheter. After introduced into the narrow portion, the stent is released from the catheter and expanded to be attached to an inner wall of a lumen such as a blood vessel. In case of PTCA (percutaneous transluminal coronary angioplasty), the stent is expanded following a blood vessel expanding operation by inflation of a balloon set on a housing inner wall. The stent is called a balloon expandable stent and formed by the use of a metal such as stainless steel or tantalum.

On the other hand, in order to prevent rupture of an aneurysm which may result in a subarachnoid hemorrhage or the like, blood supply to the aneurysm is stopped. As one of such techniques, use is made of embolization in which a metal coil, such as a platinum coil, is implanted into the aneurysm so as to form a blood clot. However, it is pointed out that a part of the blood clot may possibly be released from the metal and carried by a bloodstream to a periphery to block a blood vessel. In order to avoid this, consideration is made about a covered stent technique in which the aneurysm is embolized by the use of a graft. In this case, simultaneously when the stent is released from the catheter, the stent is expanded by its own spring function to press the graft against a blood vessel wall. Such stent is called a self expandable stent. For the self expandable stent, a material having an excellent spring characteristic is desired.

The superelastic Ti—Ni alloy is characterized in that, at a temperature above a reverse transformation finish temperature (Af point) at which reverse transformation of the alloy starting from a reverse transformation start temperature (As point) is finished, the alloy which has been deformed under an external load is recovered into an original shape simultaneously when the external load is released and that recoverable deformation reaches about 7% in case of an elongation strain. The As point means a shape recovery start temperature while the Af point means a shape recovery finish temperature (shape recovery temperature). For use as the stent, a hoop-shaped stent is formed into a size slightly greater than the lumen where the stent is to be placed. The stent is reduced in diameter and mounted to the catheter. Simultaneously when the stent is released from the catheter, the stent is spontaneously recovered into its original hoop diameter to be brought into tight contact with the lumen such as a blood vessel. Thus, the alloy has the Af point not lower than a living body temperature and always exhibits superelasticity at the living body temperature (around 37° C.).

As well as the above-mentioned merits, such superelastic stent has several demerits, such as occurrence of damage in the blood vessel wall, a positioning error in placement, lack in deliverability, and so on due to its spontaneous shape recovery characteristic. Therefore, it is difficult to use the superelastic stent in a blood vessel system such as a coronary system.

An example of a shape memory alloy used as a temperature-sensitive actuating device is described in Non-Patent Document 1 or the like. There are many examples, such as wind direction adjustment of an air conditioner, a damper of a microwave oven, and a ventilating hole. However, most of the examples utilize an R phase obtained by aging or thermomechanical treatment of the Ti—Ni alloy. The reverse transformation start temperature is about 60° C. On the other hand, an attempt for a high-temperature operating device to which this invention is applicable is described in Non-Patent Document 2. In this document, an operating temperature not lower than 100° C. is obtained by applying high strain to the Ti—Ni alloy. However, there are problems that the applied strain is large and that the operating sensitivity is low. Therefore, practical application is not yet realized.

The stent for PTCA is preferably made of a metal material having a low elastic limit, which hardly damages the blood vessel and is excellent in deliverability. However, there is left a problem that a pressing force (expanding force) against a lumen wall after expansion is weak. As means to solve the problem, a stent using a shape memory alloy is proposed. Patent Document 6 describes that a Ti—Ni—Nb alloy, to which this invention is related, is applied to a stent. Patent Document 6 describes that the stent made of a Ti—Ni—Nb shape memory alloy and having a low Young's modulus upon shape recovery and a high Young's modulus upon shape deformation under an external load is obtained when the ratio of stress on loading to the stress on unloading at the respective inflection points on a stress-strain curve in alloy deformation is at least about 2.5:1. This stent exhibits superelasticity at the living body temperature after it is released from the catheter but does not sufficiently solve the above-mentioned problem (arbitrariness in positioning) as required in PTCA.

In Patent Document 7, the present inventors have proposed a stent closely related to this invention. Specifically, proposal is made of the stent which exhibits no shape memory at the living body temperature during insertion into the living body and exhibits superelasticity after shape recovery by inflation of a balloon. In the embodiment of Patent Document 7, it is described that the stent made of a Ti—Ni alloy or a Ti—Ni—X alloy (X=Cr, V, Cu, Fe, Co, or the like) is subjected to strong deformation to thereby elevate a recovery temperature. However, problems are left in shape recovery characteristics after application of strain and adaptability to a slot shape.

Patent Document 1: U.S. Pat. No. 3,174,851
Patent Document 2: JP S58-161753 A
Patent Document 3: JP S63-171844 A
Patent Document 4: JP S63-14834 A
Patent Document 5: U.S. Pat. No. 4,770,725
Patent Document 6: JP H11-42283 A
Patent Document 7: JP H11-99207 A
Non-Patent Document 1: K. Otsuka and C. M. Wayman: Shape Memory Materials, CAMBRIDGE University Press (1998)
Non-Patent Document 2: D. Goldstein, E. Alexweiner: Nitinol-Based Fuse Arming Component, NSWXTR88-340 (1980)

DISCLOSURE OF THE INVENTION

Problem to be Solved by the Invention

In view of solving the above-mentioned problems, it is a technical object of this invention to provide a Ti—Ni—Nb alloy device which is a shape memory device excellent in response characteristics.

Means to Solve the Problem

The present inventors have found out that, by selecting heat-treatment conditions and strain-application conditions, a Ti—Ni—Nb shape memory alloy is extremely excellent in response characteristics and is applicable to a high-temperature actuating device for emergency and security and a medical device such as a stent.

According to this invention, there is provided a Ti—Ni—Nb alloy device which comprises a Ti—Ni—Nb alloy and whose transformation is finished at a temperature lower than 10° C. after start of reverse transformation.

In this invention, the content of Nb is preferably 0-15 at %, more preferably 3 at % 15%, further preferably 6-9 at %.

In this invention, the Ti—Ni—Nb alloy device preferably comprises an alloy containing at least 3 at % Nb and applied with a strain of 8% after heat treatment in terms of an elongation strain.

In the Ti—Ni—Nb alloy device according to this invention, any one of the above-mentioned Ti—Ni—Nb alloy devices preferably has a reverse transformation start temperature of 100° C.

In this invention, any one of the above-mentioned Ti—Ni—Nb alloy devices preferably has a reverse transformation start temperature higher than 37° C. and finishes transformation at a temperature lower than 5° C. By these temperatures, a Ti—Ni—Nb alloy device for a biomedical material is obtained.

According to this invention, any one of the above-mentioned Ti—Ni—Nb alloy devices has two or more reverse transformation temperatures with a seamless structure by changing one or both of a shape memory treatment temperature and an applied strain in a lengthwise direction.

Effect of the Invention

According to this invention, it is possible to provide a Ti—Ni—Nb alloy device which is a shape memory device excellent in response characteristics.

BRIEF DESCRIPTION OF THE DRAWING

FIG. 1 A view showing a heat cycle DSC curve for a test piece of a Ti-47Ni—6Nb alloy treated at 400° C. for one hour and applied with a strain of 13%.

BEST MODE FOR EMBODYING THE INVENTION

Now, an embodiment of this invention will be described.

(a) At first, alloy compositions and strain application will be described.

A Ti-50 at % Ni alloy depicted at No. 1 in Table 1, a Ti-48.5 at % Ni-32 at % alloy depicted at No. 2, a Ti-47 at %-6 at % alloy depicted at No. 3, a Ti-42 at % Ni-9 at % alloy depicted at No. 4, and a Ti-42 at %-15 at % alloy depicted at No. 5 were subjected to high-frequency induction melting, hot working, and cold working to obtain wires having a diameter of ø1.0 mm. Each wire was heat treated at 400° C. for one hour. Thereafter, an elongation strain $\epsilon$=0-15% was applied and then a load was released. For each test piece, transformation temperatures were measured. A temperature difference ($\Delta T$) from a reverse transformation start temperature to a reverse transformation finish temperature was obtained as a shape recovery sensitivity. The result is shown in Table 1.

As shown in Table 1, a comparative alloy No. 1 had a shape recovery sensitivity $\Delta T$ of 20° C. at $\epsilon$=0%, 15° C. at $\epsilon$=8%, 15° C. at $\epsilon$=10%, 15° C. at $\epsilon$=13%, and 15° C. at $\epsilon$=15%. Thus, rapid improvement in recovery sensitivity by strain application was not observed. On the other hand, each of the alloys Nos. 2 to 4 according to this invention had a recovery sensitivity of 30, 38, and 40° C. at $\epsilon$=0%, 9, 8, and 8° C. at $\epsilon$=8%, 6, 5, and 5° C. at $\epsilon$=10%, 5, 5, and 40° C. at $\epsilon$=13%, and 5, 4, and 4° C. at $\epsilon$=15%. The alloy No. 5 according to this invention had a recovery sensitivity of 40° C. at $\epsilon$=0%, 6° C. at $\epsilon$=8%, and 4° C. at $\epsilon$=10%. From the above-mentioned result, the alloys Nos. 2 to 5 according to this invention are improved in recovery sensitivity at $\epsilon$=8% or more. The alloy No. 5 in Table 1 lacks some mechanical feature and was therefore broken at $\epsilon$=13% or more. Therefore, this alloy could not be used as a test piece for characteristic evaluation.

FIG. 1 is a view showing a result of heat cycle DSC measurement for a test piece of the alloy No. 3 with a strain of $\epsilon$=13% applied thereto. From the result in FIG. 1, it is seen that reverse transformation after strain application is shifted towards a high temperature and $\Delta T$ is small and that the reverse transformation temperature after re-heating approximates to that with an applied strain of zero. This shows that the applied strain is cancelled simultaneously with heating to the reverse transformation finish temperature and, therefore, the device of this invention is an extremely excellent shape memory device.

TABLE 1

| No. | composition (at %) | | | heat treatment (° C. × time) | shape recovery sensitivity $\Delta T$ (° C.) | | | | |
| --- | --- | --- | --- | --- | --- | --- | --- | --- | --- |
| | Ni | Ti | Nb | | $\epsilon$ = 0% | $\epsilon$ = 8% | $\epsilon$ = 10% | $\epsilon$ = 13% | $\epsilon$ = 15% |
| 1 | 50 | 50 | 0 | 400 × 1 | 20 | 15 | 15 | 15 | 15 |
| 2 | 48.5 | 48.5 | 3 | 400 × 1 | 30 | 9 | 6 | 5 | 5 |

TABLE 1-continued

| | composition (at %) | | | heat treatment | shape recovery sensitivity ΔT (° C.) | | | | |
|---|---|---|---|---|---|---|---|---|---|
| No. | Ni | Ti | Nb | (° C. × time) | ε = 0% | ε = 8% | ε = 10% | ε = 13% | ε = 15% |
| 3 | 47 | 47 | 6 | 400 × 1 | 38 | 8 | 5 | 5 | 4 |
| 4 | 46 | 42 | 9 | 400 × 1 | 40 | 8 | 5 | 4 | 4 |
| 5 | 46 | 42 | 15 | 400 × 1 | 40 | 6 | 4 | — | — |

(b) Next, the heat-treatment conditions and the strain application will be described.

Table 2 shows the Af point and ΔT for test pieces Nos. 6, 7, and 8 after strain application in case where heat treatment was carried out under a different condition of 500° C. for one hour. As shown in Table 2, (Af, ΔT) of the alloy No. 6 were (85, 20) at ε=0%, (92, 15) at ε=8%, (98, 15) at ε=10%, (102, 15) at ε=13%, and (106, 15) at ε=15%. The alloy No. 7 had the values (60, 40) at ε=0%, (64, 10) at ε=8%, (82, 5) at ε=10%, (102, 5) at ε=13%, and (118, 5) at ε=15%.

The No. 8 alloy of this invention had the values (18, 40) at ε=0%, (23, 8) at ε=8%, (28, 5) at ε=10%, (42, 4) at ε=13%, and (58, 4) at ε=15%.

In Table 2, No. 7 is a Ti—Ni—Nb alloy of the same composition as No. 3 in Table 1. It is understood that, by changing the heat-treatment conditions, a shape memory device high in sensitivity exceeding 100° C. is obtained. No. 8 has an Af point of 18° C. at an applied strain of zero and exhibits superelasticity at a living body temperature of 37° C. After a strain of 13% is applied, the As point is shifted to 38° C. so that no superelasticity appears at the living body temperature. Thus, it is possible to provide a medical device which does not exhibit shape recovery during insertion into a living body but exhibits shape recovery only by heating after placement. The heating is controllable to a temperature (42° C.) such that no adverse effect is given to cells in the body.

TABLE 2

| | composition (at %) | | | heat treatment | Af and ΔT (° C.) | | | | | | | | | |
|---|---|---|---|---|---|---|---|---|---|---|---|---|---|---|
| | | | | | ε = 0% | | ε = 8% | | ε = 10% | | ε = 13% | | ε = 15% | |
| No. | Ni | Ti | Nb | (° C. × time) | Af | ΔT | Af | ΔT | Af | ΔT | Af | ΔT | Af | ΔT |
| 6 | 49.5 | 50.5 | 0 | 500 × 1 | 85 | 20 | 92 | 15 | 98 | 15 | 102 | 15 | 106 | 15 |
| 7 | 47 | 47 | 6 | 500 × 1 | 60 | 40 | 64 | 10 | 82 | 5 | 102 | 5 | 118 | 5 |
| 8 | 47.5 | 46.5 | 6 | 400 × 1 | 18 | 40 | 23 | 8 | 28 | 5 | 42 | 4 | 58 | 4 |

(c) Next, graded characteristics will be described.

As described above, the shape recovery temperature in the same alloy device can be selected by the heat-treatment conditions and the strain application conditions. Table 3 shows a Ti-47 at % Ni-6 at % Nb alloy as an alloy No. 9 and a Ti-47.5 at % Ni-6 at % Nb alloy as an alloy No. 10.

The alloy No. 9 was subjected to cold working and then to heat treatment at 500° C. for one hour throughout its entire length. A part of the alloy was again subjected to heat treatment at 700° C. for one minute. Swaging was carried out throughout the entire length to apply a strain of 13% in cross-section ratio. For the alloy No. 10, a wire material having a diameter ø 1.09 mm at a part A and a diameter ø 1.15 mm at a part B was used. Heat treatment at 400° C. for one hour was carried out throughout the entire length. Thereafter, area reduction was performed into ø 1.0 mm (applied strain: 8% at the part A, 13% at the part B). The transformation temperatures were obtained by DSC measurement. The alloy No. 9 shown in Table 3 had the Af point (° C.) of 78° C. at the part A and 95° C. at the part B. The alloy No. 10 had the Af point (° C.) of 23° C. at the part A and 42° C. at the part B. Thus, graded functions are achieved in each of the alloys Nos. 8 and 10.

TABLE 3

| | composition (at %) | | | grading conditions | | Af point (° C.) | |
|---|---|---|---|---|---|---|---|
| No. | Ni | Ti | Nb | heat treatment | strain application | part A | part B |
| 9 | 49.5 | 50.5 | 0 | entire length: 500° C., 1 hr. (A) end portion: 700° C., 1 min. (B) | entire length: 13% applied | 78 | 95 |

TABLE 3-continued

| composition (at %) | | | grading conditions | | Af point (° C.) | |
|---|---|---|---|---|---|---|
| No. | Ni | Ti | Nb | heat treatment | strain application | part A | part B |
| 10 | 47 | 47 | 6 | entire length: 400° C., 1 hr. | (A): 8% applied (B): 13% applied | 23 | 42 |

(d) Next, an applicable range of this invention will be described.

In the Ti—Ni—Nb alloy, the effect of elevating the recovery temperature by strain application become remarkable with an increase in amount of Nb added. However, excessive addition of Nb degrades plastic workability. Application of a high strain leads to decrease in amount of shape recovery like the Ti—Ni alloy. The Ti—Ni—Nb alloy exhibits shape recovery of 80% or more at a strain of 8% or less and shape recovery of 60% at a strain of 15%. However, at a strain of 20%, the recovery was smaller than 50%. Therefore, in this invention, the amount of Nb added is 3 at % or more, preferably 6-9 at %. The applied strain is 8% or more, preferably 10-15%. A shape memory alloy most suitable in this invention is a Ti—Ni—Nb alloy but may be an alloy containing a fourth element such as Fe, Cr, V, and Co.

INDUSTRIAL APPLICABILITY

As described above, the shape memory device according to this invention is high in shape recovery sensitivity and is most suitable as a high-temperature operating device and a biomedical device.

The invention claimed is:

1. A Ti—Ni—Nb alloy device which comprises one of a Ti—Ni—Nb alloy and a Ti—Ni—Nb—X alloy, wherein X is at least one metal selected from the group consisting of Fe, Cr, V, and Co,
   wherein transformation of said device is finished at a temperature difference smaller than 10° C. after a start of reverse transformation,
   wherein said Ti—Ni—Nb alloy comprises 46.5 to 50.5 at % Ti, 6 to 15 at % Nb, and a balance of 50 at % or less of Ni,
   wherein at least one of a shape memory treatment condition and a strain applied to the alloy device are changed with respect to portions of the device in a lengthwise direction thereof such that the Ti—Ni—Nb alloy device has a seamless structure with different reverse transformation temperatures in the respective portions thereof,
   wherein said shape memory treatment condition includes a shape memory treatment temperature and a shape treatment time, and
   wherein said alloy device has a strain ranging between 8% and 15% in terms of an elongation strain after a heat treatment so as to have a temperature difference, ΔT, smaller than said alloy having no strain in a temperature range between 4 to 10° C., said temperature difference being from a reverse transformation start temperature, As point, to a reverse transformation finish temperature, Af point.

2. The Ti—Ni—Nb alloy device according to claim 1, wherein said alloy comprises 46 to 48.5 at % Ni.

3. The Ti—Ni—Nb alloy device according to claim 2, wherein the Ti—Ni—Nb alloy device is a high-temperature operating device and has a reverse transformation start temperature of at least 100° C. in at least one of the respective portions thereof.

4. The Ti—Ni—Nb alloy device according to claim 2, wherein the Ti—Ni—Nb alloy device is a device for a biomedical material, has a reverse transformation start temperature higher than 37° C. in at least one of the respective portions thereof, and finishes transformation at a temperature lower than 5° C. in said portion.

5. The Ti—Ni—Nb alloy device according to claim 1, wherein the Ti—Ni—Nb alloy device is a high-temperature operating device and has a reverse transformation start temperature of at least 100° C. in at least one of the respective portions thereof.

6. The Ti—Ni—Nb alloy device according to claim 1, wherein the Ti—Ni—Nb alloy device is a device for a biomedical material, has a reverse transformation start temperature higher than 37° C. in at least one of the respective portions thereof, and finishes transformation at a temperature difference smaller than 5° C. in said portion.

7. The Ti—Ni—Nb alloy device according to claim 1, wherein both of a shape memory treatment condition and a strain applied to the alloy device are changed with respect to portions of the device in a lengthwise direction thereof, such that the Ti—Ni—Nb alloy device has a seamless structure with different reverse transformation temperatures in the respective portions thereof.

8. The Ti—Ni—Nb alloy device according to claim 7, wherein the alloy is a Ti—Ni—Nb—X alloy, wherein X is at least one metal selected from the group consisting of Fe, Cr, V and Co.

9. The Ti—Ni—Nb alloy device according to claim 1, wherein the alloy is a Ti—Ni—Nb—X alloy, wherein X is at least one metal selected from the group consisting of Fe, Cr, V and Co.

10. The Ti—Ni—Nb alloy device according to claim 1, wherein a shape memory treatment condition is applied to the alloy device which changes with respect to portions of the device in a lengthwise direction thereof, such that the Ti—Ni—Nb alloy device has a seamless structure with different reverse transformation temperatures in the respective portions thereof.

11. The Ti—Ni—Nb alloy device according to claim 1, wherein a strain is applied to the alloy device which changes with respect to portions of the device in a lengthwise direction thereof, such that the Ti—Ni—Nb alloy device has a seamless structure with different reverse transformation temperatures in the respective portions thereof.

* * * * *